United States Patent
Lazenby

(10) Patent No.: US 7,549,963 B2
(45) Date of Patent: Jun. 23, 2009

(54) MULTI STAGE BEAMFORMING

(75) Inventor: John C. Lazenby, Fall City, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 455 days.

(21) Appl. No.: 11/089,996

(22) Filed: Mar. 25, 2005

(65) Prior Publication Data

US 2006/0241490 A1  Oct. 26, 2006

(51) Int. Cl.
A61B 8/00 (2006.01)

(52) U.S. Cl. .................. 600/443; 600/447

(58) Field of Classification Search .......... 600/443, 600/445, 447; 73/618; 128/916
See application file for complete search history.

(56) References Cited

U.S. PATENT DOCUMENTS

| | | | |
|---|---|---|---|
| 5,111,824 A | 5/1992 | Lazenby et al. | |
| 5,627,799 A * | 5/1997 | Hoshuyama | 367/121 |
| 5,718,230 A | 2/1998 | Chapman et al. | |
| 5,882,307 A * | 3/1999 | Wright et al. | 600/442 |
| 6,309,356 B1 | 10/2001 | Ustuner et al. | |
| 6,443,896 B1 * | 9/2002 | Detmer | 600/445 |
| 6,447,452 B1 | 9/2002 | Liu et al. | |
| 6,527,720 B1 | 3/2003 | Ustuner et al. | |
| 6,599,245 B1 | 7/2003 | Ma et al. | |
| 6,685,641 B2 | 2/2004 | Liu | |
| 6,806,623 B2 | 10/2004 | Petersen et al. | |
| 2008/0027321 A1 | 1/2008 | Lazenby | |

OTHER PUBLICATIONS

"A method for design of digital beamformer with prescribed main beam width and sidelobe level" Do-Hong, Tuan; Russer, Peter. Munich University of Technology, Institute for High-Frequency Engineering. Munich 2003.*
U.S. Appl. No. 12/240,764, filed Sep. 28, 2008.
U.S. Appl. No. 12/240,806, filed Sep. 28, 2008.

* cited by examiner

Primary Examiner—Eric F Winakur
Assistant Examiner—Michael T Rozanski

(57) ABSTRACT

Beamforming for N elements in performed in log(N) steps of complexity O(N). The signals measured at each element are treated as a receive beam formed by that element with a beam width equal to the element pattern or the width of the transmit illumination. In each of multiple stages, the number of elements is halved by effectively doubling the pitch. The number of beams formed by each element is doubled by narrowing the beam width by a factor of 2 in $\sin(\theta)$. Since steering and focusing are separated, a single set of delays are applied to each element signal individually prior to the multi-stage beam forming for each finite depth. The data is in a sector format, but by using two beamforming steps, data in a Vector® format is provided.

15 Claims, 1 Drawing Sheet

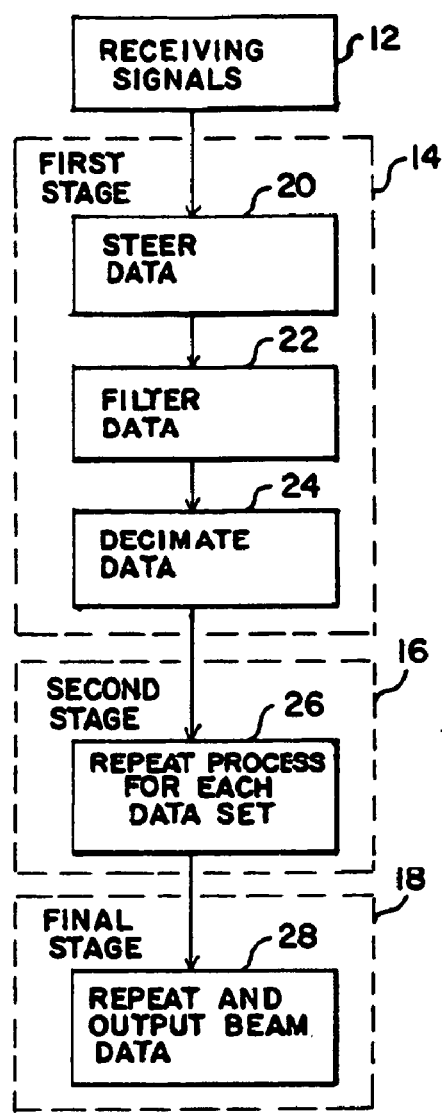
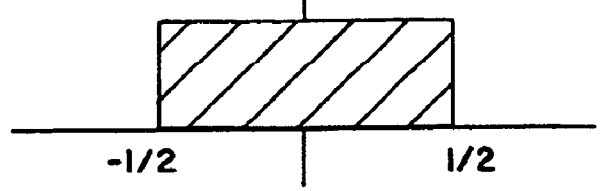
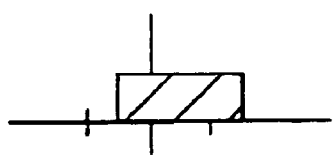
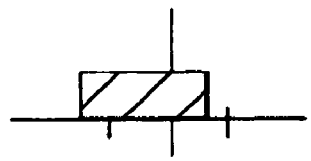
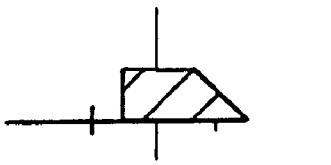
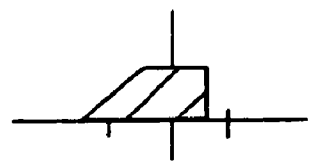
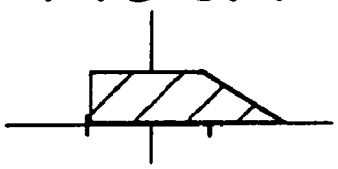
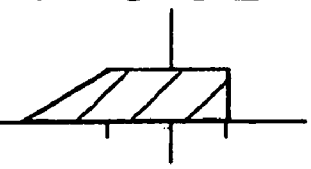
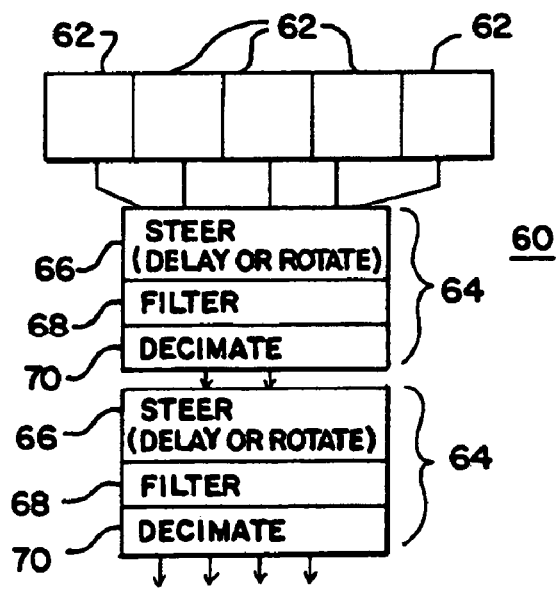

MULTI STAGE BEAMFORMING

BACKGROUND

The present invention relates to beamforming. In particular, ultrasound signals from a patient are beamformed to provide values representing one or more spatial locations.

Acoustic energy is transmitted as an acoustic beam into a patient. Echoes are received and transduced to electrical signals. The received signals are relatively delayed and apodized. The delayed and apodized signals are then summed together. The summed value represents a spatial location along a receive beam. By altering the delay and/or apodization profile as a function of time, a plurality of beamformed values representing a line or beam are formed in response to a given transmission. To scan a two or three dimensional region, the process is repeated along a plurality of different scan lines. The scan process may be increased by transmitting and/or receiving a plurality of separate beams at a same time.

To increase the scan rate, a plane wave covering a large region of the patient is transmitted. A plurality of receive beamformers are used in parallel to form receive beams along different scan lines in response to the same transmit. Alternatively, a Fourier transform is applied to the data received at each element of an array over time. After processing in the frequency domain, an inverse transform generates data representing the different locations in the scanned region. For example, see U.S. Pat. No. 6,685,641, the disclosure of which is incorporated herein by reference. A temporal Fourier transform is applied to radio frequency echo signals from each element. The signals are then phase rotated. A spatial Fourier transform is then applied, followed by a complex interpolation. An inverse spatial-temporal Fourier transform provides the image data.

BRIEF SUMMARY

By way of introduction, the preferred embodiments described below include methods and systems for beamforming. Multiple stages of beamforming in the time domain efficiently generate data representing different spatial locations. Each stage reduces data representing the effective number of elements and increases an effective number of beams. For example, two different delay profiles are applied to steer in two different directions within a previous stage's beamwidth. After filtering and decimation, a number of effective beams is increased and a number of effective elements for each beam decreases. By applying multiple stages, up to one beam per element is provided for generating an image.

In a first aspect, a method is provided for beamforming data from a region received at an array. Signals are received at a plurality, N, of elements. First and second sets of data responsive to the signals are filtered. The first and second sets of the filtered data are decimated. The filtering and decimating are repeated for each of the first and second sets of the decimated data.

In a second aspect, a method is provided for beamforming data from a region received at an array. N signals are received at respective N elements. The N signals are a data set. A first stage is operable to increase by a second factor from the data set to a number X of data sets and reduce the N signals by a first factor to M signals in each of the X data sets. A second stage is operable to increase from the X number of data sets by a fourth factor to Y number of data sets and reduce the M signals by a third factor to O signals in each of the Y data sets. The first, second, third and fourth factors are the same or different than each other.

In a third aspect, a system is provided for beamforming ultrasound data from a region. A first plurality of delays is operable to be connected with a respective plurality of transducer elements. The first plurality of delays is operable to steer signals from the plurality of transducer elements in first and second different directions. The signals steered in the first direction are a first set of data, and the signals steered in the second direction are a second set of data. At least a first filter connects with the first plurality of delays and is operable to filter the first and second sets of data. At least a first decimator is operable to decimate the first and second sets of the filtered data. A second plurality of delays is operable to be connected with the at least the first decimator. The second plurality of delays is operable to steer the first set of decimated data in third and fourth different directions and is operable to steer the second set of decimated data in fifth and sixth directions. At least a second filter connects with the second plurality of delays. The at least the second filter is operable to filter the sets of data steered in the third, fourth, fifth and sixth directions. At least a second decimator is operable to decimate the sets of filtered data steered in the third, fourth, fifth and sixth directions.

In a fourth aspect, a system is provided for beamforming ultrasound data from a region. A first stage is operable to output at least two sets of data in response to an input set of data. The at least two sets of data correspond to different steering directions, and each has at least half as many values as the input set of data. A second stage is operable to output at least four sets of data in response to the at least two sets of data. The at least four sets of data correspond to different steering directions for a first one of the at least two sets of data and different steering directions for a second one of the at least two sets of data. Each of the at least four sets of data has at least half as many values as each of the at least two sets of data.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a flow chart diagram of one embodiment of a method for beamforming;

FIG. 2 is a graphical representation of one embodiment of data in a spatial frequency domain;

FIGS. 3A and B are graphical representations of one embodiment of two sets of data steered in different directions in the spatial frequency domain;

FIGS. 4A and B are graphical representations of one embodiment of two sets of data after filtering;

FIGS. 5A and B are graphical representations of one embodiment of two sets of data after decimation; and FIG. 6 is a block diagram of one embodiment of a beamformer and elements.

DETAILED DESCRIPTION OF THE DRAWINGS AND PRESENTLY PREFERRED EMBODIMENTS

Beamforming for N elements may be performed in log(N) steps of complexity O(N). The signals measured at each element are treated as receive beamformed by that element with a beam width equal to the element pattern or the width of the transmit illumination. Multiple stages are then applied to narrow the beamwidth. At each stage, the number of elements is halved by effectively doubling the pitch. The number of beams formed by each element is doubled by narrowing the beam width by a factor of 2 (in sin(θ)).

Various implementations are possible. In one implementation, continuous wave beamforming with an infinite focus is provided. Separating steering and focusing, a single set of delays is applied to each element signal individually prior to the multi-stage beamforming for focus at finite depths. These delays may be dynamic. In one implementation, the data represents a sector format of beams originating from the center of the array. However, by using two beamforming steps, the data represents a Vector® format of beams which originate from a virtual apex behind the array. Beamforming for a two-dimensional array uses separate steering in elevation from steering in azimuth. In another implementation, a virtual point source transmit is accommodated by creating vector data with a virtual apex at the virtual point source location. In that format, the transmit arcs of constant propagation time correspond to the arcs of data output from the beamformer at a given time or distance. Each of these implementations is discussed in sequence below.

FIG. 1 shows a method for beamforming data from a region received at an array. The method corresponds to continuous wave beamforming, but is applicable to other implementations. The method includes receiving signals 12 and applying two or more stages 14, 16, 18. Additional, different or fewer acts may be provided. For example, a total of seven stages are provided for an array of 128 elements. As another example, only two stages are applied to provide beamformed data or data for other purposes. Other orders of acts may be used.

In act 12, signals are received at a plurality, N, of elements. For example, each element in a receive aperture transduces acoustic energy to electric signals at a given time. The signals provide a data set. For the N elements, the data set includes N signals. The signals are analog signals or are converted to digital signals.

In one implementation, the signals are continuous wave (CW) signals received in response to continuous wave transmission. For far field CW imaging, the signal from each element of the array is represented by a single complex number, but other representations may be used. Each single element has a very wide spatial bandwidth, so signals from a wide variety of directions contribute to the signal. Normalizing the signals to a spatial sampling frequency of 2, the spatial frequencies extend from $-1$ to $+1$. All possible signals are within the normalized range. However, the information of interest is assumed to be within the frequency range from $-\frac{1}{2}$ to $\frac{1}{2}$ as represented in FIG. 2. Greater or lesser symmetrical or asymmetrical ranges of the information of interest may be used. For a wider initial bandwidth, interpolation may be used to provide signals from virtual elements between each actual element, bringing the spatial bandwidth down to the range $-\frac{1}{2}$ to $\frac{1}{2}$.

In act 14, a first beamforming stage is applied. The beamforming stage is operable to increase the number of data sets and reduce the number of signals in each data set. For example, a single data set of the signals from each element is input. The number of data sets is increased by a factor, such as increasing the one data set by a factor of 2 to two data sets or effective beams. The number of signals, such as 128 signals for a 128 element array, is reduced by a factor, such as reducing from 128 signals in one data set by a factor of $\frac{1}{2}$ to 64 signals in each of two data sets. The factors for reduction of signals and increasing the number of data sets are equal, different, related or unrelated, such as increasing the number of data sets by 2 but decreasing the number of signals by $\frac{1}{3}$.

The first beamforming stage is applied by performing steering act 20, filtering act 22 and decimation act 24. Additional, different or fewer acts may be provided. The beamformer stage increases the number of data sets and corresponding effective beams, such as by steering each of one or more input data sets in two or more different directions. The beamformer stage reduces the amount of data in each output data set by filtering and decimation to decrease the beam width represented by each set of data.

In act 20, the signals are steered in two or more different directions. Different delay or phase shift profiles are applied to the same data in sequence or parallel. The signals may be steered right and left at equal distances on either side of straight ahead. For three directions, the signal may be steered right, left, and straight ahead. A greater number of directions and associated data sets are formed by using a greater number of delay or phase shift profiles.

The directions are established by the delay or phase shift profiles, such as corresponding to beams at the centers of each half of a beam width represented by the input data set (i.e., steering symmetrically right and left). For example, the frequencies associated with the data are shifted in different directions. In one embodiment, the phase profiles of [ . . . , exp(-2*pi*j*2/8), exp(-2*pi*j*1/8), exp(2*pi*j*0/8), exp(2*pi*j*1/8), exp(2*pi*j*2/8), . . . ] and [ . . . , exp(2*pi*j*2/8), exp(2*pi*j*1/8), exp(2*pi*j*0/8), exp(-2*pi*j*1/8), exp(-2*pi*j*2/8), . . . ] are multiplied with the input signals. Other phase profiles may be used. The phase profile is applied in a pattern across the face of the array or all effective elements. The phase of the signals for each element or effective element is rotated.

After steering, the number of sets corresponds to the number of directions or profiles applied to the input data set, such as outputting two data sets steered in two different directions. FIGS. 3A and B show the data set represented in FIG. 2 steered equally to more positive and more negative frequencies, corresponding to left and right steering. Two different data sets are output in response to the input data set.

In act 22, the sets of data are filtered using a spatial filter. The signals steered in one direction are filtered, and the signals steered in another direction are filtered. The filtering removes information associated with regions or steering away from the direction of interest. A band pass or low pass filter response is used. For example, a low pass filter is operable to reduce information at high positive frequencies for the set of data shown in FIG. 3A, and the same or different low pass filter is operable to reduce information at high negative frequencies for the set of data shown in FIG. 3B. FIGS. 4A and B show signals resulting from an approximation of low pass filtering the data sets of FIGS. 3A and B, respectively. The low pass filter passes signals with |freq|<¼ and rejects signals with |freq|>¾. The net effect of the steering and filtering is equivalent to two filters centered at $-\frac{1}{4}$ and $\frac{1}{4}$. The left hand filter passes signals from $-\frac{1}{2}$ to 0, while the right hand filter passes signals from 0 to $\frac{1}{2}$. Bandpass filtering is alternatively provided, so as to perform the steering and filtering in a same act.

The filtering corresponds to any number of taps with any possible passband characteristics. For example, an 8 tap low pass finite impulse response filter has coefficients: $-0.0242$, $-0.0496$, $0.1329$, $0.4341$, $0.4341$, $0.1329$, $-0.0496$, and $-0.0242$. This filter provides $-37$ dB of out-of-band rejection, resulting, approximately, in $-37$ dB peak grating lobes. Longer or shorter filters are possible, but may result in additional multipliers. Out-of-band rejection for some possible longer filters include: taps=8, peaklobe=−37.5; taps=9, peaklobe=−39.2; taps=10, peaklobe=−46.2; taps=11, peaklobe=−56.7; taps=12, peaklobe=−54.5; taps=13, peaklobe=−56.4; taps=14, peaklobe=−62.9; taps=15, peaklobe=−73.1; and taps=16, peaklobe=−71.2. If an odd number of taps are used, some of the coefficients are zero in half band filters.

Once the data sets correspond to information for each of two or more steered beams with limited beam width, the data is decimated. The filtered signals in each data set are decimated. Any amount of decimation may be used, such as decimating by a factor of 2. For example, every other data value from the filtered sets of data is removed. The number of signals in each data set is reduced, such as each of two data sets shown in FIGS. 4A and B being reduced by half. The decimation increases the bandwidths of the data sets, such as doubling the bandwidth. FIGS. 5A and B show the increased bandwidth provided by decimation in each of the two data sets of filtered information in FIGS. 4A and B, respectively. The frequency band |freq|<¼ doubles in width to |freq|<½, and signals in the band |freq|>¾ alias into that same bandwidth. The filtering suppresses the aliased signals.

The same amount of data is output after decimation as input for steering, but is divided into more data sets. Greater or lesser decimations or amount of output data relative to the amount of input data may be provided. After the first stage is applied in act 14, the number of data sets is increased, corresponding to an increase in the number of effective beams. The amount of data in each data set decreases.

In act 16, a second beamforming stage is applied. The second beamforming stage increases the number of data sets and reduces the number of signals in each data set. For example, the two data sets from application of the first stage 14 are input. The number of data sets is increased by a factor, such as increasing the two sets of data by a factor of 2 to four data sets or effective beams. The number of signals, such as 128 total signals of 64 values in each of two sets, is reduced by a factor, such as reducing from 64 signals in each of two data sets by a factor of ½ to 32 signals in each of four data sets. The factors for reduction of signals and increasing the number of data sets are equal, different, related or unrelated, such as increasing the number of data sets by 3 but decreasing the number of signals by ½. The factors are the same or different than used in application of the first stage 14.

In act 26, the second beamforming stage includes repeating the filtering and decimating for each of the sets of the decimated data output from the first stage 14. For each repetition of filtering and decimating, a number of values in each data sets decreases and a number of data sets increases. For example, the bandwidths of each of the input left and right steered sets have the same bandwidth as the original data received in act 12, but with only half as many channels in each of those sets. So after another repetition in act 26, data sets for four steering directions (left, left), (left, right), (right, left), (right, right) are provided with only a quarter as many channels or numbers of signals in each set.

In act 28, additional beamforming stages are applied, including a final beamforming stage 18. Each additional stage increases the number of data sets and decreases the number of signals in each data set. Each input data set is steered in two or more different direction. Since a plurality of data sets is input, the steering results in an increased number of effective beams representing different spatial locations. Each stage narrows the effective field of each beam by dividing the effective field into two or more data sets. In one embodiment, the final beamforming stage provides a single value for each data set. The signal value represents a beam at a focal depth.

Each data set corresponds to a different beam. Where the received data includes N signals, the final stage outputs N beams or spatial frequency bins that are spread equally over the original frequency band (−½, ½). In an example with 128 elements and associated received signals, seven beamforming stages provide 128 output beams spaced throughout a region scanned by the transmit beam. The beam numbers go from 0 at the far left to 127 at the far right. Beam 64 is just to the right of straight ahead, and straight ahead is along the y axis at spatial frequency=0. A greater number of signals may be provided in one or more of the final data sets.

For pulsed wave operation, the received pulsed wave signals have a relatively large bandwidth as compared to continuous wave (CW) signals. Unlike CW signals, the pulsed wave signals are represented by a time sequence of values and not by a single complex value. Steering in act 20 as well as the repetitions in different stages is performed by applying sets of delays or different delay profiles. In one embodiment, the channel-to-channel or signal-to-signal relative delay amount is about equal to the 2*pi*j/8 phase rotation for the highest temporal frequency contained in the signal. For a large bandwidth signal, with the highest frequency being equal to twice the center frequency, the channel-to-channel or signal-to-signal relative delay is 1/16 of the period of the center frequency (a relative delay of about 12.5 nanoseconds for 5 MHz center frequency). For each channel, the delay applied is an integer multiple of 1/16 of the period of the center frequency. If sampling the signal at 16 times the center frequency, the delays may be integer numbers of samples. Greater or lesser relative delays may be provided. The delay profile is a linear ramp across all the signals or channels of a given data set in one embodiment, but non-linear or varying delay profile may be used.

A lesser sampling rate may be used, such as where analog-to-digital converters operate at a slower rate. For example, the signals are sampled at 4 times the center frequency. Half band or other filters up-convert to four times the center frequency. For example, three zero values are inserted between each signal, and then the signals are low pass filtered. The resulting signals provide values as if sampled at 16 times the center frequency. After beamformation, the beamformed signals are decimated back to 4 times the center frequency or lower, such as for complex representations in narrowband applications.

Pulsed wave signals are typically associated with two or three-dimensional imaging. The beamformer stages discussed above, where the delay or phase profile is a linear ramp, form beams in equal sin(θ) focused at infinity. Delay profiles that are non-linear and time-varying forms beams that are focused at finite depths and dynamically focused, respectively, may be used. These delay profiles are more difficult to implement than the fixed linear ramp.

In other embodiments, to obtain information for discrete or finite depths, a delay profile is applied to the signals prior to filtering in act 22 in the first stage, such as applying the delays to the received signals after act 12 and before the first beamforming stage in act 14. The delay profile corresponds to focusing delays for the depth of interest. The remaining beamforming stages are applied without the additional delay profile for the finite depth. For dynamic focusing, the delay profile varies for each finite depth or as a function of time. For each depth, the beamforming process shown in FIG. 1 is repeated, but with a different finite depth delay profile. Applying the focusing delays before the first beamforming stage in act 14 involves making an approximation where focusing the beam is separated from steering the beam. This approximation can degrade the focusing at large steering angles, but for modest steering angles, the simplification may justify a small degradation.

The delay profile for finite depth focusing corresponds to a desired lens with a focus at the desired depth. For example, the approximate depth delay profile includes quadratic focusing delays of the form $-x^2/(2Rc)$ for the depth R where x is the element position and c is the speed of sound. The greatest delays are applied to the elements at the center of the array. Other quadratic or non-quadratic focusing functions may be used. For a given delay profile, a set of focused beams for the scanned region is provided at the depth R still in equal $\sin(\theta)$. If the quadratic focusing delays are dynamic, a sector image is formed with beams in equal $\sin(\theta)$.

A Vector® scan format is provided in other embodiments. Vector® image beamformed data is generated with a two step beamforming process. The first step focuses or defocuses the input signals to make the signals appear to have been measured at virtual point receivers at some backset. For each depth, a set of delays are applied to the received data. The set of delays or delay profile are a function of a backset of an origin point from the elements. The backset is on an opposite side of the elements of the array than the region being scanned. The backset is the distance between the actual and virtual arrays. For example, quadratic delays, such as $x^2/(2*backset*c)$ are applied to the signals. Other delay functions, such as a linear delay ramp, a square root function, or a quadratic cosine or sine function, may be used.

After applying the fixed set of delays, the beamforming process discussed above for FIG. 1 is performed. Steering delays, filtering and decimation are repeated to form values for the given depth along a plurality of beams. By putting a fixed set of delays on the received signals for all or most of the elements and applying the multi-stage beamforming process, the signals represent signals as if received from an array at the backset. The values are signals representing information measured from virtual point receivers located along an arc of radius equal to the backset, spaced in equal $\sin(\theta)$. The values have aligned phases.

In a second step, the virtual point receiver data (i.e., values output from the first step representing virtual point receiver information) is used to form a sector image. Since the data received for forming the sector image is relative to the virtual array, the beamformed output corresponds to a vector image relative to the physical array. The delay profile applied for forming the sector image is relative to a distance from the virtual array rather than the actual array and taking into account the curvature of the virtual array. For quadratic delays of the form $-x^2/(2*Rp*c)$, Rp is given by $1/Rp=1/Rv-1/backset$, where backset is the backset distance and Rv is the distance from the virtual array to the arc for each depth being beamformed.

The two step process is repeated for each depth of interest. For example, dynamic delays for finite depths are used. Beamformed values representing different spatial locations within a Vector® region are provided.

The Vector® or sector beamformed values represent spatial location along a lateral extent. The lateral extent is a function of the sample interval and element pitch. For example, using the sample interval of 16 times the center frequency of 5 MHz, a channel-to-channel relative delay equal to the sample interval, and an element pitch of one half wavelength (at the center frequency), steering angles of 14.5 degrees away from the center provide a lateral extent less than 30 degrees wide. The sine of the maximum steering angle is equal to 2 * (channel-to-channel relative delay)*c/pitch. To make a wider image, the pitch is decreased or the sample interval is increased. To decrease the pitch without using a different array, signals are interpolated between the actual elements. To increase the maximum steering angle to 45 degrees (sin=0.707), a pitch of sqrt(2)/16 wavelengths is desired. Alternatively, a lesser maximum steering angle is used.

The transmit event used to receive the data in act 12 is a plane wave or diverging wave. A plane wave is associated with a virtual point source at infinity. A diverging wave is associated with a virtual point source at other locations. Other waves may be used, such as a narrow or focused wave with a wide field. The receive beamforming is independent of or dependent on the transmitted field. For example, the receive beamforming is performed without consideration of the location of the point source as long as the receive scan format is within the transmitted field. As another example, the set of delays for the sector or Vector® beamforming correspond to a virtual transmit point. The backset is selected to correspond to the virtual point source of the transmit wave. The transmit wave fronts correspond to the arcs of data output from the beamformer at a given time. The receive beams are formed along the path of propagation of the transmit wave. The receive beamformed values at any given point in time or depth lie along the transmit wave front.

In some embodiments, the beamformed data is used to form additional beams, such as synthetic compounding (i.e., compounding with phase information) or compounding data received in response to different transmissions. For example, the virtual point source for sequential transmissions varies. The output data is transformed or converted from the sampling grid used for a particular virtual point source to a fixed sampling grid to be used for compounding.

Beamforming is provided for two or three dimensional imaging. The transducer array is one dimensional (e.g., linear or curved) or multi-dimensional (e.g., 2D or 1.5D). For a multi-dimensional array, the elements are distributed on a plane or curved surface along two dimensions. Multi-dimensional array may be used to scan a three-dimensional volume. The receive beams are formed at different location through the volume. The receive beamforming of FIG. 1 may be applied to a multidimensional array.

In one embodiment, the signals received in act 12 are from an array of transducer elements arranged in the two dimensions of azimuth and elevation. In act 20, steering is performed in both azimuth and elevation. Four steering directions are used: upper left, upper right, lower left, and lower right, resulting in four data sets. The filtering of act 22 is performed in both the azimuth and elevation spatial directions. The signals are then decimated spatially in each of azimuth and elevation by a factor of two, resulting in a reduction of signals by a factor of four. As before, the factors for reduction of signals and increasing the number of data sets are equal, different, related or unrelated.

The second beamforming stage 16 increases the number of data sets and reduces the number of signals in each data set. For example, the four data sets from application of the first stage 14 are input. The number of data sets is increased by a factor, such as increasing the four sets of data by a factor of four to 16 data sets or effective beams. The number of signals in each data set, such as 64 signals in each of four sets (for a total of 256 signals), is reduced by a factor, such as reducing from 64 signals in each of four data sets by a factor of ¼ to 16 signals in each of 16 data sets. The factors are the same or different than used in application of the first stage 14.

In act 28, additional beamforming stages are applied, including a final beamforming stage 18. Each additional stage increases the number of data sets and decreases the number of signals in each data set. In an example with 256 elements in a 16 by 16 array and associated received signals, four beamforming stages provide 256 output beams in a 16 by 16 array spaced throughout a three dimensional region scanned by the transmit beam. A greater number of signals may be provided in one or more of the final data sets.

In another implementation, an approximation is made to separate the steering in azimuth from steering in elevation. The receive beamforming of FIG. 1 is performed in two passes to provide beams distributed along azimuth and elevation dimensions at each given depth. In the first pass, the receive beamforming (i.e., the filtering, decimating and repeating the filtering and decimating) is performed with steering in one dimension, such as along the azimuth dimension. Data from each of the elements is delayed and steered as if forming an image along one dimension. Each data value output represents a sum of data along a perpendicular dimension. In the second pass, the receive beamforming is performed with steering in the perpendicular dimension, such as along the elevation dimension.

Since each beamforming stage performs steering, the elevation and azimuth steering terms are decoupled. For example, an array of elements includes a plurality of 16×16 sub arrays. For each sub-array, 256 delay lines are used for sector or Vector® focusing. Sixteen 16-channel multi-stage receive beamformers connect with the 256 delay lines. The sixteen multiple stage receive beamformers each output 16 to 48 values. The 16 to 48 values are input to another level of multi-stage beamformers for a second pass with steering along the different dimension. 256 to 2304 beams are output, arranged in a sector format. Additional layers of multi-stage beamforming may be used to convert the sector scan of the volume into a Vector® or linear scan format.

Using the two pass hardware configuration discussed above for volume scanning may limit two dimensional imaging with a one dimensional array to 16 beams. The first pass of multi-stage beamformers (e.g., for steering in azimuth) form the same set of 16 beams corresponding to the 16 beams formed by the second pass of beamformers (e.g., for steering in elevation). Alternatively, additional multiple stage beamformers, multiplexers and/or buffers are used to allow operation for both a long one dimensional array and multi-dimensional arrays with the same hardware.

FIG. 6 shows a system 60 for beamforming ultrasound data from a region. The system 60 includes an array of elements 62 connected with a plurality of beamforming stages 64. Additional, different or fewer components may be provided, such as one or more analog or digital delays connected between the elements 62 and the first beamforming stage 64 for finite focus depth. Any number of beamforming stages 64 is provided, such as two, three, four, five, six, seven or more.

The beamforming stages 64 and/or any additional delays are implemented in an application specific integrated circuit, but may be implemented in part or fully as a processor, field programmable gate array, analog circuit, digital circuit or combinations thereof. In one embodiment, each beamforming stage 64 is a separate application specific integrated circuit with or without an integrated multiplexer for connecting with elements 62, other beamforming stages and/or a medical ultrasound imaging system.

The array of elements 62 is a one or multi-dimensional array. The elements 62 connect directly or indirectly through one or more multiplexers or transmit/receive switches to the first beamforming stage 64.

Each beamforming stage 64 includes a plurality of delays or phase rotators 66 for steering, one or more filters 68 and one or more decimators 70. Additional, different or fewer components may be provided. In one embodiment, the beamforming stages 64 operate on all of the input data. Alternatively, the array is sub-divided and different components or devices implement a particular beamforming stage for the relevant sub-array. For example, a 16-input device includes 16 dynamic delay lines. The delay line outputs may be optionally interpolated to 32 or 64 values. Different beamforming stages 64 have the same or different number of components as other stages 64, such as later or a final beamforming stage having more components for processing a greater number of data sets.

The delays or phase rotators 66 include a plurality of delays or phase rotators 66, such as one delay for each input channel. In one embodiment, the delays 66 are implemented as multipliers with one or more buffers. For example, about 200 hundred multipliers implement delays for 16 input signals. An input channel includes an element 62, a data value from a data set or other source of data. For the first beamforming stage 64, the delays or phase rotators 66 connect with respective elements 62 for relative delaying between signals from different elements 62. In one embodiment, separate pluralities of delays or phase rotators 66 receive the same data sets for steering signals in different directions. Alternatively, a buffer or memory is used for sequential application of different delay or phase rotation profiles to the same input data. After application of different profiles, two sets of data associated with different steering are output.

The filter 68 is a finite impulse response filter with any number of taps. Infinite impulse or other now known or later developed filters may be used. The filter 68 connects with the plurality of delays or phase rotators 66 directly or through one or more multiplexers or buffers. The filter 68 is operable to filter the input sets of data. A separate filter 68 is used for each set of data or a single filter 68 sequentially filters each set of data.

In one embodiment, the filter 68 is an 8 tap filter. Where the beamforming stage 66 is associated with 16 input values, such as for a 16 element sub-array, 512 multipliers are provided. Given symmetric filter coefficients, 256 multipliers may be used. With interpolation of input data to 64 values for generating 64 beams at a higher spatial sampling rate, 3072 multipliers or 1536 with coefficient symmetry are provided. With the multipliers used for the delays, the total number of multipliers is on the order of N log(N) where N is the number of elements and corresponding number of output beams.

Interpolation improves the performance of the filter 68 if used to increase the spatial sampling rate. The input spatial bandwidth is maintained, but the filter transition bandwidth may be broader. For example, an 8 tap filter with passband edge at ⅛ and stopband edge at ⅞ has a stopband rejection of 63 dB, while an 8 tap filter with passband edge at 1/16 and stopband edge at 15/16 has a stopband rejection of 90 dB. Other interpolation and filtering may be used. The signals are also up-sampled in time.

The decimator 70 is a switch, processor, filter or other device for removing or reducing data. The decimator 70 decimates each of the input data sets, such as decimating by half each data set. Non-symmetric or other decimation rates may be used.

The first beamforming stage 64 is operable to output at least two sets of data in response to an input set of data from the elements 62. The output sets of data correspond to different steering directions, and each output set of data has fewer values or signals, such as at least half as many values, as the input set of data. The output sets of data are passed to a second or subsequent beamforming stage 64. The second beamforming stage 64 is operable to output at least two sets of data in response to each input set of data, such as outputting four sets of data in response to two input sets. The output sets of data correspond to different steering directions, such as four different steering directions for four sets of data. Each output set of data has fewer values or signals, such as at least half as many values, as respective ones of the input sets of data. The number of steering directions per input data set, number of output data sets, decimation factor, steering directions or deviation from center, or other factors are the same or different between data sets in the same beamformer stage 64 or the same or different between beamformer stages 64.

Additional beamforming stages 64 further reduce the amount of data in each set of data and increase the number of beams or data sets. A final beamforming stage 64 outputs beamformed data. The beamformed data is responsive to the previous beamforming stages 64. In one embodiment, the final beamforming stage 64 outputs data sets each having a single value representing a different spatial location. Each value represents a beam at a given depth. The number of beams or values is substantially equal to the number of values in the input set of data or elements 62.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for ultrasound beamforming data from a region received at an array, the method comprising:
   receiving signals at a plurality, N, of elements, the signals responsive to a region of a patient;
   filtering first and second sets of data responsive to the signals, first and second pass bands of the filtering for the first and second sets of data, respectively, being a function of first and second different beam steering directions, respectively;
   decimating the first and second sets of the filtered data;
   repeating the filtering and decimating for each of the first and second sets of the decimated data, each of the first and second sets corresponding to a beam wherein the repetition narrows a beamwidth associated with each of the respective beams of the first and second sets, the repeating providing multiple data sets for each of the first and second data sets, the data of each of the multiple data sets having the narrowed beamwidth relative to the respective first and second data sets; and
   generating an image as a function of the data of each of the multiple data sets.

2. The method of claim 1 further comprising:
   steering the signals in the first and second different beam steering directions;
   wherein the first set of the data corresponds to the signals steered in the first direction and the second set of the data corresponds to the signals steered in the second direction.

3. The method of claim 2 wherein receiving the signals comprises receiving continuous wave signals and wherein steering the signals comprises applying first and second sets of phase shifts to the signals.

4. The method of claim 2 wherein receiving the signals comprises receiving pulsed wave signals and where steering the signals comprises applying first and second sets of delays to the signals.

5. The method of claim 2 wherein filtering comprises applying a low pass filter, the low pass filter operable to reduce information at high positive frequencies for the first set of data and the low pass filter operable to reduce information at high negative frequencies for the second set of data.

6. The method of claim 1 wherein filtering comprises applying a low pass filter.

7. The method of claim 1 wherein, for each repetition of filtering and decimating, a number of values in each data sets decreases and a number of data sets increases, the repeating being performed until each data set comprises a single value.

8. The method of claim 1 further comprising:
   applying a delay profile to the signals prior to filtering, the delay profile corresponding to a first depth; and
   repeating the receiving, applying, filtering, decimating, and repeating the filtering and decimating for each of a plurality of depths, one of the plurality being the first depth.

9. The method of claim 8 further comprising:
   further comprising applying a same set of delays for each repetition of the repeating the receiving, applying, filtering, decimating and repeating the filtering and decimating for each of the plurality of depths, the set of delays being a function of a backset of an origin point from the elements away from the region.

10. The method of claim 9 further comprising:
    applying the same set of delays such that the origin point corresponds to a virtual transmit point.

11. The method of claim 1 wherein the elements comprise a multi-dimensional transducer array.

12. The method of claim 11 further comprising performing the filtering, decimating and repeating the filtering and decimating in two passes, a first pass being along a first dimension and a second pass being along a second dimension different than the first dimension.

13. The method of claim 1 wherein filtering comprises spatial filtering.

14. The method of claim 1 further comprising:
    generating beamformed data responsive to the repetitive filtering and decimation, wherein the first and second data sets are responsive to the same signals and represent different spatial locations, and the beamformed data corresponds to the filtered and decimated data of the first and second data sets after a final repetition of the filtering and decimation.

15. The method of claim 1 wherein the signals for each of the N elements are in a third set of data, the first and second sets being formed from the third set by filtering and decimation, each repetition reducing data representing an effective number of elements and increasing an effective number of beams.

* * * * *